US006733806B2

(12) United States Patent
Shiau et al.

(10) Patent No.: US 6,733,806 B2
(45) Date of Patent: May 11, 2004

(54) METHOD FOR PRESERVATION OF PRODUCE

(75) Inventors: Yen-Kuen Shiau, Taipei (TW); Chung-Hsun Wu, Tao Yuan (TW)

(73) Assignee: Parker Holding-Services Corp., Taipei (TW)

( * ) Notice: Subject to any disclaimer, the term of this patent is extended or adjusted under 35 U.S.C. 154(b) by 461 days.

(21) Appl. No.: 09/918,515

(22) Filed: Aug. 1, 2001

(65) Prior Publication Data

US 2003/0031811 A1 Feb. 13, 2003

(51) Int. Cl.[7] .................................................. A23B 7/015
(52) U.S. Cl. ....................................... 426/107; 426/240
(58) Field of Search ................................. 426/107, 237, 426/240; 99/451; 428/34.4

(56) References Cited

U.S. PATENT DOCUMENTS

| 5,030,510 | A | * | 7/1991 | Yokoyama et al. | 428/305.5 |
| 5,234,985 | A | * | 8/1993 | Koo et al. | 524/492 |
| 5,707,911 | A | * | 1/1998 | Rakhimov et al. | 501/128 |
| 6,051,246 | A | * | 4/2000 | Shiau et al. | 424/409 |

* cited by examiner

Primary Examiner—George C. Yeung
(74) Attorney, Agent, or Firm—Alice L. Chen; Chen Patents

(57) ABSTRACT

A method and product for preserving produce including plants comprising storing the produce and plant in a container incorporated with a spinel $AB_2O_4$ and resin mixture which emits a radiation of 3–18 and 3–30 micron wave length.

10 Claims, No Drawings

METHOD FOR PRESERVATION OF PRODUCE

BACKGROUND OF THE INVENTION

1. Field of the Invention

This invention relates to a novel method and container for the preservation of produce. More particularly, it relates to irradiation of produce with electromagnetic radiation having specific wave lengths for retaining the freshness of produce, such as vegetables, fruits, and certain plants.

2. Prior Art

Currently, vegetables are preserved in plastic bags with nitrogen, excluding oxygen to avoid spoilage. This is expensive and labor-intensive. A more recent approach to preserve food is to use irradiation to dry and store food as disclosed in U.S. Pat. No. 5,707,911. Another method is to use radioactive substances to irradiate produce and in combination with an oxygen-reactive chemical to keep food fresh, as disclosed in U.S. Pat. No. 5,030,510. The latter method is not safe in view of the radioactive substance. Thus there is a need for an economical and safe method to preserve produce.

The object of this invention is to use a mineral, spinel, to irradiate produce, thereby keeping it fresh.

Spinels are known for their antimicrobial properties as shown in applicant's U.S. Pat. No. 6,051,246. Infrared radiation is known for its beneficial effects in sterilization of food. However, no method or product in prior art is known using spinel compounds of the general formula $AB_2O_4$ as disclosed herein for preserving produce.

SUMMARY OF THE INVENTION

It has now been discovered that far-infrared radiation emitted by spinels having the general formula $AB_2O_4$ preserves the freshness of produce. The radiation should be in the wavelength range from 3–30 microns, and preferably 3–18 microns. The spinel $AB_2O_4$ powder mixed with resin is coated on a container such as a bag or box, and the fresh produce is stored in such a container.

DETAILED DESCRIPTION OF THE INVENTION

The novel component of the container of this invention is a far-infrared emitting spinel having the general formula of $AB_2O_4$, wherein A is magnesium, divalent iron, nickel, manganese, cobalt, or zinc. B is aluminum, trivalent iron, trivalent manganese, or trivalent chromium. O is oxygen. The spinel $AB_2O_4$ emits radiation in the range of wavelength from 3–30 microns, which has the desired preservation effect. It is further found that treatment with radiation in the spectral range of 3–18 microns is preferred due to its higher efficiency.

A container which may be a bag or a box of any material such as plastic, paper, or cardboard, is coated on either the inside or the outside of its walls, with spinel powder mixed with an adhesive or resin. Alternatively, powder spinel is mixed with polyethylene or other resins in the ratio of from 1:9 to 1:49, preferred ratio is 1:19.by weight. The mixture can be processed and made into a plastic bag or used as coating.

The following test was carried out:

Produce tested: Litchi, banana, apple and flower chrysanthemum was each individually stored in a plastic bag with incorporated spinel which emits radiation of 3–18 micron wave length. A control specimen is also prepared without using spinel bag.

Daily observation was made and recorded.

| Produce | Days spoilage started control | Days spoilage started spinel bag |
| --- | --- | --- |
| litchi | day 7 | day 15 |
| banana | day 5 | day 13 |
| lettuce | day 3 | day 7 |
| chrysanthemum | day 12 | day 21 |

It is seen that the produce lasts almost twice as long when stored in the spinel treated container.

We claim:

1. A container for preservation of produce having incorporated thereon a mixture of resin and powder spinel, $AB_2O_4$ wherein A is magnesium, divalent iron, nickel, manganese, cobalt, or zinc, B is aluminum, trivalent iron, trivalent manganese, or trivalent chromium, and O is oxygen.

2. The container of claim 1 wherein said spinel emits radiation in the wavelength range of 3–30 micron.

3. The container of claim 1 wherein the mixture of spinel to resin is in the ratio of from 1:9 to 1:49 by weight.

4. The container of claim 3 wherein the ratio of spinel to resin is 1:19 by weight.

5. A container for preservation of produce having incorporated thereon a mixture of resin and powder spinel, $AB_2O_4$, wherein A is magnesium, divalent iron, nickel, manganese, cobalt, or zinc, B is aluminum, trivalent manganese, or trivalent chromium, and O is oxygen.

6. The container of claim 5 wherein said spinel emits radiation in the wavelength range of 3–18 micron.

7. A process of preserving produce comprising subjecting said produce to the irradiation of a spinel $AB_2O_4$, wherein A is magnesium, divalent iron, nickel, manganese, cobalt, or zinc, B is aluminum, trivalent iron, trivalent manganese, or trivalent chromium, O is oxygen.

8. The process of claim 7 wherein the spinel irradiates in the 3–30 micron wave length.

9. The process of claim 7 wherein the B component of spinel $AB_2O_4$, is aluminum, trivalent manganese, or trivalent chromium.

10. The process of claim 9 wherein said spinel emits a radiation of 3–18 micron wave length.

* * * * *